(12) United States Patent
Schreckenberg et al.

(10) Patent No.: US 8,911,375 B2
(45) Date of Patent: Dec. 16, 2014

(54) THREE-DIMENSIONAL DERIVATION OF A PROXIMAL ISOKINETIC SHELL OF A PROXIMAL FLOW CONVERGENCE ZONE AND THREE-DIMENSIONAL PISA FLOW MEASUREMENT

(75) Inventors: Marcus Schreckenberg, Freising (DE); Georg Schummers, München (DE)

(73) Assignee: Tomtec Imaging Systems GmbH (DE)

( * ) Notice: Subject to any disclaimer, the term of this patent is extended or adjusted under 35 U.S.C. 154(b) by 471 days.

(21) Appl. No.: 13/125,617

(22) PCT Filed: Oct. 19, 2009

(86) PCT No.: PCT/EP2009/063640
§ 371 (c)(1),
(2), (4) Date: Jul. 21, 2011

(87) PCT Pub. No.: WO2010/046330
PCT Pub. Date: Apr. 29, 2010

(65) Prior Publication Data
US 2011/0282210 A1    Nov. 17, 2011

(30) Foreign Application Priority Data
Oct. 24, 2008 (DE) .......................... 10 2008 053 073

(51) Int. Cl.
*A61B 8/06* (2006.01)
(52) U.S. Cl.
CPC ........................................ *A61B 8/06* (2013.01)
USPC ............ 600/454; 600/453; 600/437; 600/456
(58) Field of Classification Search
None
See application file for complete search history.

(56) References Cited

U.S. PATENT DOCUMENTS

| | | | |
|---|---|---|---|
| 4,913,159 A | 4/1990 | Gardin et al. | |
| 7,270,635 B2 * | 9/2007 | Pedrizzetti et al. | 600/454 |
| 2002/0151794 A1 | 10/2002 | Li | |
| 2005/0165308 A1 * | 7/2005 | Jacob et al. | 600/443 |
| 2007/0255136 A1 * | 11/2007 | Kristofferson et al. | 600/437 |
| 2008/0085043 A1 * | 4/2008 | Watanabe et al. | 382/131 |
| 2013/0261458 A1 * | 10/2013 | Wei et al. | 600/441 |

FOREIGN PATENT DOCUMENTS

| | | |
|---|---|---|
| DE | 102007020314 A1 | 10/2007 |
| DE | 202008003245 U1 | 7/2008 |
| WO | 03/060553 A2 | 7/2003 |
| WO | 03/073046 A1 | 9/2003 |

OTHER PUBLICATIONS

International Search Report issued Dec. 22, 2009 by European Patent Office re: International Application No. PCT/EP2009/063640 citing US 2002/151794, WO 03/060553, WO 03/073046, DE 10 2007 020314, US 4,913,159 an DE 20 2008 003245.
Shiota et al., "Direct Measurement of Three-dimensionally Reconstructed Flow Convergence Surface Area and Regurgitant Flow in Aortic Regurgitation", American Heart Associate, 96, 1997, pp. 3687-3695.
Utsunomiya et al., "Doppler Color Flow 'Proximal Isovelocity Surface Area' Method for Estimating Volumn Flow Rate: Effects of Orifice Shape and Machine Factors", JACC, vol. 17, No. 5; 1991, pp. 1103-1111.

\* cited by examiner

*Primary Examiner* — Long V. Le
*Assistant Examiner* — Bradley Impink
(74) *Attorney, Agent, or Firm* — Cantor Colburn LLP

(57) ABSTRACT

The invention relates to a device and to a method for adaptive three-dimensional derivation of a proximal isokinetic shell of a proximal flow convergence zone that forms in an observation area in a moving fluid, wherein the magnitude of the velocity of the fluid at each point of the proximal isokinetic shell is identical and equal to a velocity reference value, the method including: a) preparing locally distributed velocity measurements in a surrounding area of the observation area, the measurements representing at least one directional component of the local velocity of the fluid in a respective measurement direction, b) preparing an approximation surface as an initial proximal isokinetic shell) in such a way that the entire flow, at least substantially, in the flow convergence zone penetrates the approximation surface, c) establishing a plurality of approximation points on the approximation surface, d) determining the respective velocity measurements at the respective approximation points, e) calculating a corrected velocity ($v_{kkJ}$) at each approximation point as a function of the velocity measurement indicated there, the respective measurement direction; and the respective surface normal, f) determining a correction direction by comparing the corrected ($v_{kkJ}$) velocity with the velocity reference value, g) optionally shifting the approximation points in the respective correction direction to new positions, h) acquiring a new approximation surface such that the same at least approaches the new positions of the approximation points, and i) repeating steps c) through h) until the change of the new approximation surface is sufficiently minimal compared to the old approximation surface.

12 Claims, 7 Drawing Sheets

THREE-DIMENSIONAL DERIVATION OF A PROXIMAL ISOKINETIC SHELL OF A PROXIMAL FLOW CONVERGENCE ZONE AND THREE-DIMENSIONAL PISA FLOW MEASUREMENT

TECHNICAL FIELD

The invention relates to the field of measuring the flow of a fluid, in particular blood in the human body, by utilizing a proximal isokinetic shell (PIS) forming in the fluid.

The invention relates in particular to methods for deriving such a PIS as well as for measuring the flow at the PIS as well as corresponding devices therefor.

BACKGROUND

The invention can be applied inter alia in the medical field to detect and, if necessary, evaluate for example mitral insufficiencies with the help of the condition of the PIS. Here, also the blood flow coming systolically through the closed mitral valve which, however, is leaking, is decisive. Although data acquired by means of three-dimensional color Doppler sonographic examinations show this undesired reflux, a quantitative evaluation and, hence, the medical relevance is difficult for various reasons. The reflux behind the mitral vale on the side of the atrium, which is also referred to as "jet", generally has such high flow rates that it is not possible to determine the true velocity of this flow when carrying out a measurement with pulsed ultrasound due to Doppler aliasing. Directly in front of the mitral valve, on the side of the ventricle, a so-called convergence zone forms, which is characterized in that respective layers of the same velocity are generated, which are referred to as PIS (proximal isokinetic shell or proximal isovelocity surface). These layers are superimposed like onion's skin, wherein the magnitude of the velocity increases towards the opening. Due to this layering the gradient of the velocity by definition exists only perpendicularly to the orientation of the surfaces of these skins and, consequently, also the flow rate is known, i.e. perpendicular to the surface of a PIS. If both the surface area (Area A) as well as the magnitude of the velocity are known for a PIS, the flow can be calculated from the product of these two quantities. This method is known as PISA method.

However, it is inherent in all Doppler measurements that it is not possible to measure the respective velocity vector of a flow particle, but only the projection of this velocity vector on the direction of the measuring beam. Thus, only the component of the velocity vector in the direction of the ultrasonic head is known, however not the component perpendicular thereto. If the correct direction of the flow can be acquired from other sources, such as a second ultrasound head, MRI data or vessels' geometry, for example, it is basically possible to carry out an angle correction. In practice, however, when using a color Doppler device, the angle to be corrected may not be much larger than 45° since otherwise the original color Doppler measurement is disturbed too much.

Hitherto known methods of PISA flow measurement do not depart from actually measured PIS forms, but from forms which easily can be modeled mathematically. The prevalent models are a hemisphere and a half-ellipsoid. For example, in the case of a hemisphere, it is sufficient to measure the radius (along the ultrasound beam) in order to calculate the PISA, while in the case of a half-ellipsoid, additionally the lengths of the further semi-axes have to be measured. An example for this is mentioned in Utsunomiya T, Ogawa T, Doshi R, Patel D, Quan M, Henry W L, Gardin J M., Doppler color flow 'proximal isovelocity surface area' method for estimating volume flow rate: effects of orifice shape and machine factors. J Am Coll Cardiol. 1991; 17:1103-1111.

In T. Shiota, M. Jones, A. Delabays, X. Li, I. Yamada, M. Ishii, P. Acar, S. Holcomb, N. G. Pandian, and D. J. Sahn, Direct Measurement of Three-dimensionally Reconstructed Flow Convergence Surface Area and Regurgitant Flow in Aortic Regurgitation: In Vitro and Chronic Animal Model Studies. Circulation, Nov. 18, 1997; 96(10): 3687-3695, a semi-quantitative method was described, in which the volume enclosed by a PIS (slice summation) was multiplied by the velocity.

However, the two above-mentioned methods are not sufficiently precise in practice. Due to angle errors between the ultrasound beam and the flow direction the direct measurement of the PIS is generally erroneous: the apparent course of the PIS, i.e. the surface with constant velocity, which can be identified for example by means of the color change in Doppler aliasing, does not correspond to the reality due to this angle error. For example, a PIS which in reality is perfectly hemispherical, is shown e.g. in a shape which approximates a half-ellipsoid in the three-dimensional Doppler dataset. In particular in the case of complexly shaped PIS, such as those that can be caused by a crescent-shaped version of the mitral valve, which cannot be described by means of simple shape models, this leads to significant measurement errors.

BRIEF SUMMARY

The invention seeks to avoid the above-mentioned problems and to provide a method with which a PIS for any flow pattern can be correctly derived. A method is provided with which a PISA flow measurement can be carried out even for flow patterns of any shape. The invention also suggests corresponding devices with which the above-mentioned methods can be carried out.

The invention provides a method for deriving a PIS in an observation area, among which are counted a leaking mitral valve or a vessel lesion, for example. Such method, as a first step, prepares locally distributed velocity measurements in a surrounding area of the observation area, which represent at least one directional component of the local velocity of the fluid in a respective measurement direction. "To prepare" the velocity measurements means here that either values already measured and stored in an earlier method over the entire domain of interest are used, or that the values are measured specifically for this method. In a second step, an approximation surface is provided as an initial, i.e. initial apparent, proximal isokinetic shell PIS in such a way that the entire flow in the flow convergence zone, at least substantially, penetrates the approximation surface. This means that the approximation surface covers the entire observation area and, thus, that the entire flow present there is captured. "To provide" here can mean that the approximation surface is formed using the geometric information of the dataset containing the velocity measurements. Alternatively, it is also possible to choose an approximation surface such that it is particularly easy to represent it mathematically, for example, or—possibly based on empirical values—that it can be expected that the feasibility of the method is particularly good. Therefore, in the case referred to as alternative, the second step can also be carried out before the first step.

Then, a plurality of approximation points is established on the approximation surface, and, at the approximation points, the respective velocity measurements are determined. "To determine" can mean read-only access to velocity measurements already taken, but also measuring the respective velocities. Then, a corrected velocity is calculated at each approximation point, dependent on the velocity measurement taken there on the respective measurement direction and the respective surface normal. This allows also for a correction of the velocity where the corrected velocity does not necessarily have to be perpendicular to the approximation surface, which can be helpful in particular in the first iteration steps. The direction of the corrected velocity can be derived using the velocity gradient and the direction of the measuring beams.

Then, the respective corrected velocity is compared with the velocity reference value, and a correction direction is thus determined so as to be able to shift the approximation points in the respective correction direction in the course of an iteration. Said approximation points are then possibly located at new positions—if the correction direction is not a "zero vector".

Finally, a new approximation surface is acquired such that it at least approaches the new positions of the approximation points. To this end, for example the shifted approximation points can be directly used, or a majorization is carried out by means of a regression function. Alternatively, it is also possible to form the new approximation surface by a spline model. In this case, it is also possible to regularize or smooth the surface.

This method is repeated from establishing a plurality of approximation points up to here until the method is converged, i.e. until the change of the new approximation surface compared to the old approximation surface is sufficiently minimal. In so doing it is also possible to keep the approximation points used in a previous iteration step in one or more subsequent iteration steps.

As soon as the method is converged, the approximation surface thus determined can be assumed as the actual proximal isokinetic shell and be displayed, stored or otherwise used. The observation of the surface geometry of the PIS is of diagnostic value insofar as it allows for, for example, relatively exact conclusions regarding the type or extent and/or geometry of the flow in the case of a defect of the mitral valve, for example.

The invention further provides a three-dimensional PISA flow measurement in a PIS. Here, the course of action is the same as discussed above until the precise, exact PIS is determined from the initially available apparent PIS. The three-dimensional PISA flow is then determined by multiplying the surface area of the exact PIS by the velocity reference value, as a result of which the PISA flow can be exactly calculated three-dimensionally.

According to a preferred embodiment of the two above-mentioned methods, the respective differential angle between the respective measurement direction and the respective surface normal onto the approximation surface at the approximation points is determined and taken into consideration in order to calculate the corrected velocity.

Here, the corrected magnitude of the velocity is advantageously calculated in that the original measurement of the velocity is at this point divided by the cosine of the differential angle, wherein preferably the respective differential angle is beforehand reduced by a value of correction, which decreases with increasing iteration, such as an exponential function. The differential angle is hereby only slightly modified after many iteration steps, while at the beginning of the iteration it is still modified more heavily.

It is preferred that the correction direction points away from the flow convergence zone if the corrected velocity is larger than the velocity reference value, and that it points towards the flow convergence zone if the corrected velocity is smaller than the velocity reference value. Furthermore, there is preferably no correction of the position of the approximation points if the difference between the corrected velocity and the velocity reference value is within a certain tolerance range.

An advantageous variant of the shifting of the approximation points is to use a predetermined step width for shifting the points. Alternatively, the step width can also be proportional to the difference between the reference velocity and the corrected magnitude of the velocity, which in some cases may lead to a faster convergence of the method.

It is particularly easy to carry out the methods according to the invention if each approximation point—at least in certain sections of the iteration—is shifted along the respective surface normal onto the approximation surfaces.

As has already been described at the beginning, the velocity vectors can only be determined sufficiently reliably up to an angle of about 45° to the measuring direction. This means that initially the apparent PIS at the edges cannot be determined at all or that it can be determined only very imprecisely. Therefore, it is advantageous to check after each iteration step whether further approximation points can be used in addition to or possibly in exchange for a part of the approximation points already used, which approximation points are closer to the edge of the PIS. By using also these additional approximation points, it is possible to enlarge the respective approximation surface and to determine more precisely the surface area of the resulting, adaptively approached PIS. The further course of the PIS can be extrapolated; its borders can be determined from additional image information, such as B mode.

A particularly practicable and inexpensive method for determining the respective velocities comprises using pulsed ultrasound beams, which determines also the spot where the respective velocities are measured. Here, the velocities are determined preferably using a plurality of measuring angles, i.e. by scanning the measurement range. Alternatively, however, it is also possible to determine the velocities by means of MRI or other image-recording modalities. A particularly efficient method results from the use of a color Doppler ultrasound device.

The problem underlying the invention can also be solved by creating a corresponding computer program product or a computer program product with the help of which a corresponding control and evaluation system of a device for deriving a PIS or of a device for calculating the PISA flow is controlled, and which implements the execution of one of the aforementioned methods. Such a computer program can be realized on a data carrier on which the computer program product is stored.

The problem underlying the invention is also solved by creating a device which a PIS can be adaptively derived three-dimensionally. Such a device comprise a storage means for storing at least one approximation surface for the PIS, a velocity reference value, a plurality of approximation points and respective velocities, and a control and evaluation system by means of which the device according to one of the above-discussed methods for the adaptive three-dimensional derivation of a PIS can be controlled.

The problem underlying the invention is also solved by means of a device for the three-dimensional PISA flow measurement, which comprises identical or similar storage means as the above-mentioned device as well as a control and evaluation system which serves to control the device according to one of the above-discussed methods for the three-dimensional PISA flow measurement.

Preferably, the aforementioned devices comprise a display device, on which at least an approximation surface and the PIS determined can be displayed. Furthermore, if necessary, further data, images or process parameters can be displayed on such a display device. Advantageously, a device according to the invention also may comprise an ultrasound measuring device, in particular a color Doppler ultrasound measuring device, with the help of which the required ultrasound data can be acquired by means of corresponding measurements. It is particularly advantageous if one of the aforementioned devices is integrated in a medical ultrasound device. In this case, a physician can carry out the respective ultrasound imaging on the patient, and the device provides him already with a precise display of the PIS, which can be a good basis for his diagnosis, as well as with further parameters, such as the PISA flow in the observation area, which, for example, can be a defective mitral valve, i.e. a mitral valve having a lesion, or a mitral valve which does not close perfectly.

BRIEF SUMMARY

Advantageous improved embodiments of the invention result from the following description of the figures, by means of which advantageous embodiments of the invention are shown. The figures show.

DETAILED DESCRIPTION

Figure 1:
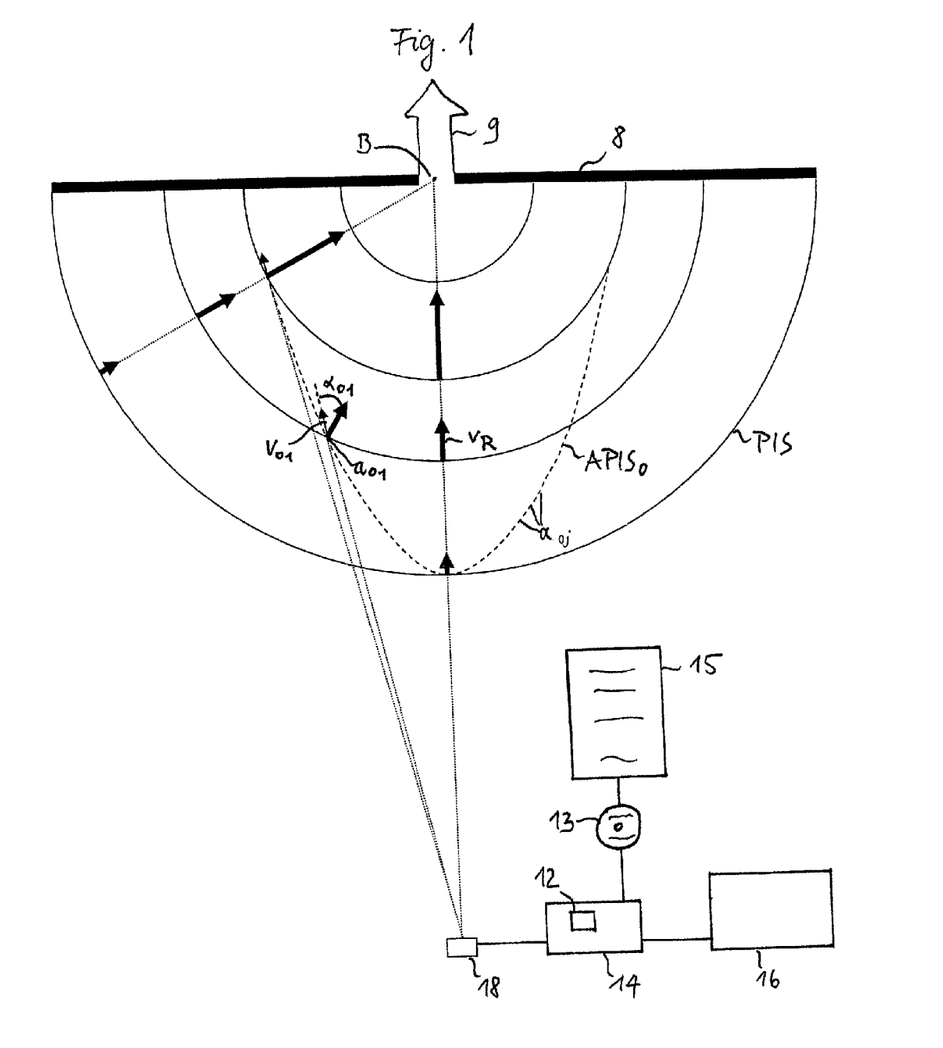
FIG. 1 a first embodiment of the devices according to the invention with a proximal flow convergence zone and an approximation surface as well as several proximal isokinetic shells, at the beginning of the iteration, FIG. 2 the approximation surface of FIG. 1 with a corrected velocity and a determined correction direction, FIG. 3 an approximation surface after the first iteration, FIG. 4 an approximation surface after the second iteration, FIG. 5 an approximation surface after the third iteration, FIG. 6 a second embodiment of the device according to the invention with an approximation surface, and FIG. 7 a flow chart for an embodiment of a method according to the invention.

FIG. 1 depicts a sector color Doppler ultrasonic head 18, which is connected to a computer 14, which serves as a control and evaluation system for carrying out ultrasonic measurement processes as well as evaluating and displaying the data acquired. The computer 14 has at least one storage unit 12 for storing the corresponding data, and is connected to a monitor 16 for displaying images and other data. The computer 14 can accommodate a data carrier, such as a CD ROM 13, on which a computer program 15 is stored, by means of which the computer 14 is controlled.

A defective mitral valve 8 is schematically shown, which has an opening in the center, which opening is referred to as observation area B and through which a so-called jet 9 flows. A proximal isokinetic shell PIS has to be derived for the observation area B. There are shown various PIS which, in the case of a circular hole in the mitral valve 8, have the shape of hemispheres. Here, the central cross-sections through these hemispheres are shown so that the respective true PIS have the shape of semi-circles. $APIS_0$ shows an (apparent) PIS, as it is measured by the ultrasonic head 18 due to the angle measurement errors which occur. The $APIS_0$ has approximately the shape of an ellipse and is shown in dashed lines.

Here, FIG. 1 shows the starting situation before the beginning of the derivation or iteration process, respectively, in which the velocity values measured are the same over the entire initial surface of the $APIS_0$. The thick arrows indicate the respective velocity vectors on the circular surfaces of the true PIS and not on the ellipse of the apparent PIS or $APIS_0$, respectively. According to the flow chart of FIG. 7, this apparent PIS or $APIS_0$, respectively, is initialized in a step S2, i.e. either retrieved as an image file which is already present or determined by recording with the help of the ultrasonic head 18 in a plurality of measurement directions and by carrying out an interpretation, after in a step S1 locally distributed velocity measurements have been provided in a surrounding area of the observation area B, which represent a directional component of the local velocity of the fluid in a respective measurement direction. If a second ultrasonic head were present, a further directional component could be provided with the help of said second ultrasonic head.

In this embodiment, the $APIS_0$ comprises a plurality of approximation points $a_{kj}$, which are established in a step S3, wherein each index k represents the number of iteration steps and each index j represents the consecutive number of the approximation point, i.e. in the broadest sense represents the arrangement in space. This denomination of the indices also applies to all other indexed quantities. An approximation point $a_{01}$ with temporarily subsequent corresponding approximation points and respective indexed quantities, with the help of which the adaptive or iterative derivation of the PIS is to be shown, is specifically shown in the figures.

Figure 7:
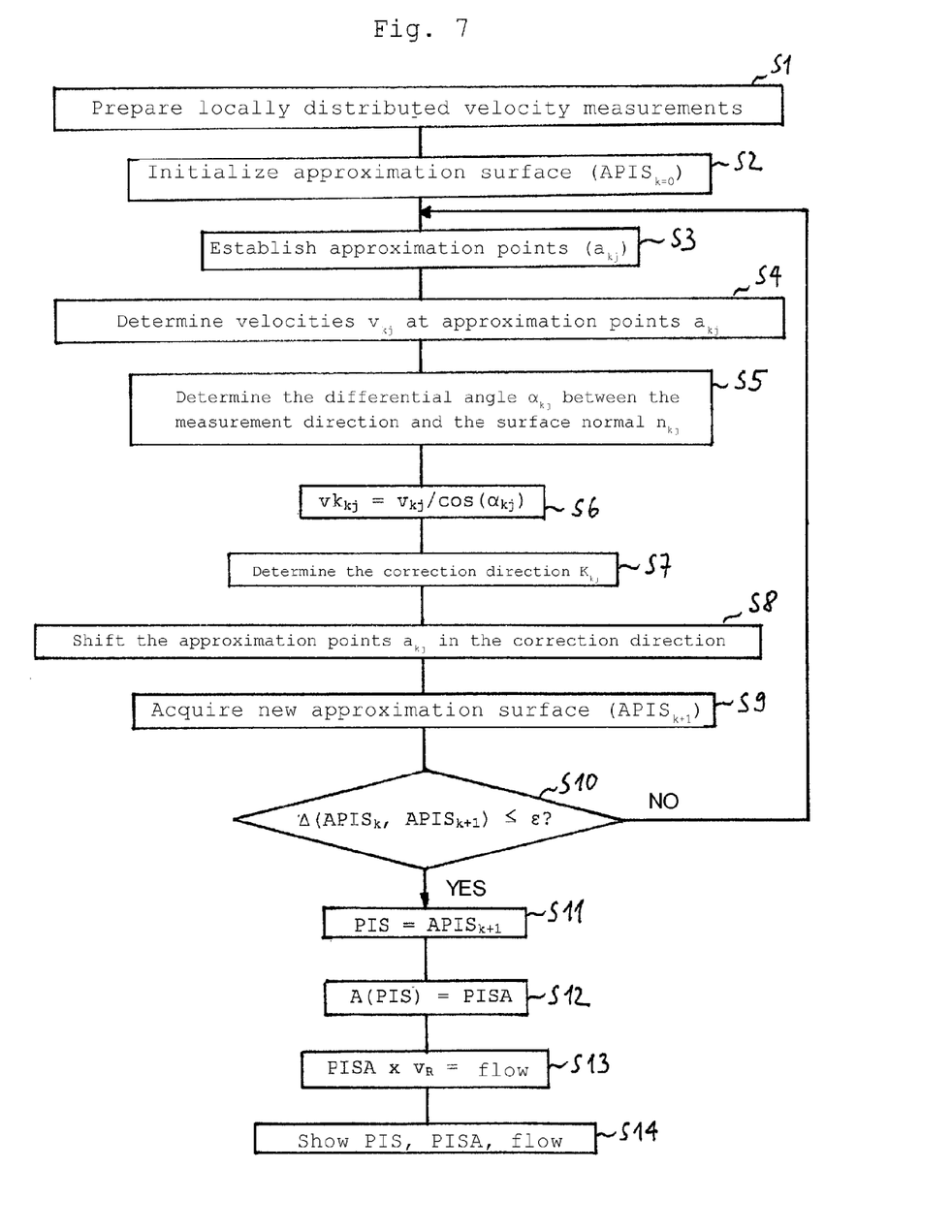

Then, in a step S4, the corresponding velocity measurement value $v_{kj}$ is determined at each approximation point $a_{kj}$, i.e. $v_{01}$ at $a_{01}$.

Figure 2:
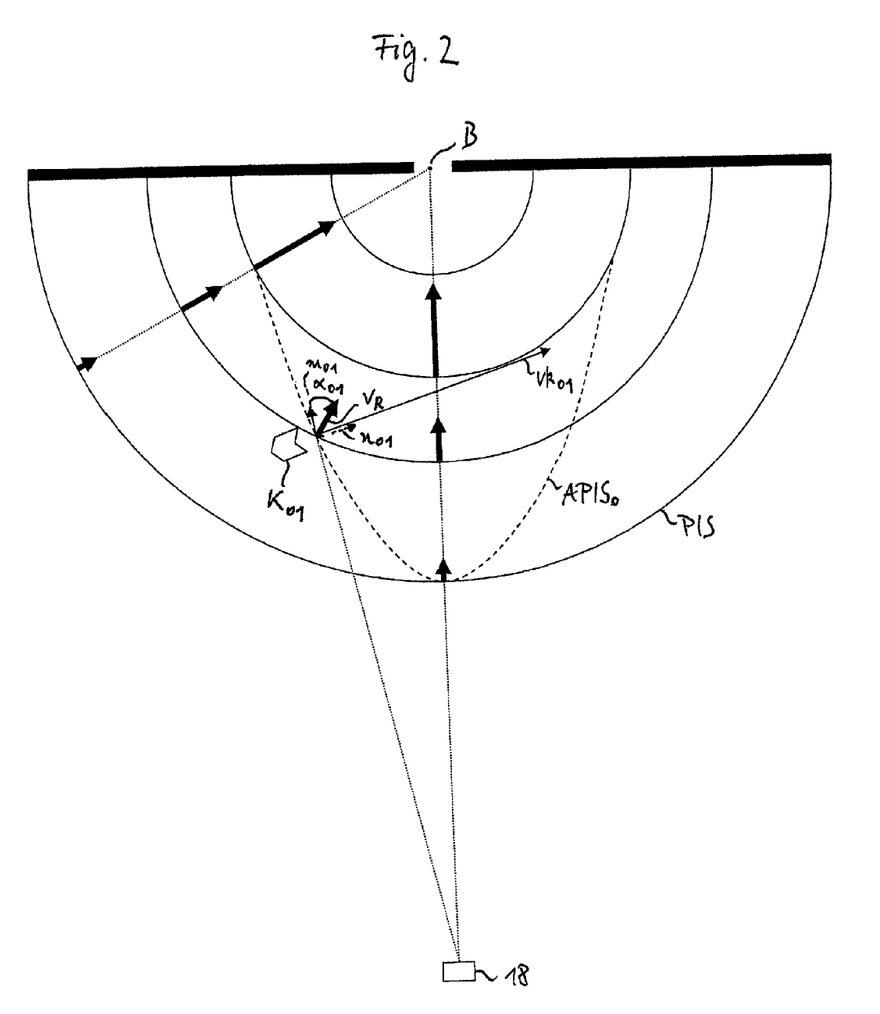

In a step S5, the differential angle $\alpha_{kj}$ between the measurement direction $m_{kj}$ of the ultrasonic head 18 and the surface normal $n_{kj}$, which is shown in dashed lines in FIG. 2, is determined, at $a_{01}$ between $m_{01}$ and $n_{01}$, i.e. $\alpha_{01}$. In a step S6, the velocity $v_{kj}$ measured is corrected by dividing it by the cosine of the differential angle $\alpha_{kj}$, assuming in this example that the true direction is perpendicular to the surface. The resulting corrected velocity $vk_{01}$ is also shown. For the first iteration steps, as an alternative to this example, it may be more favorable to assume a direction which is suitably interpolated between the surface normal and the direction towards the observation area B and/or uses a smaller scaled differential angle $\alpha_{kj}$.

Then, in step S7, a correction direction $K_{kj}$ symbolized by an arrow is determined in order to find out whether the approximation point $a_{kj}$ has to be shifted towards the outside away from the observation are B or towards the inside towards the observation area B. To this end, it is checked whether the corrected velocity $vk_{kj}$ is larger than the reference velocity $v_R$; if this is the case, the approximation point has to be shifted to the outside. Otherwise, it is shifted towards the inside. Preferably, no correction has to be made if the difference between the corrected velocity $vk_{kj}$ and the velocity reference value $v_R$ is within a certain tolerance range.

Then, in a step S8, the approximation point $a_{kj}$ is shifted towards the outside in the correction direction $K_{01}$ determined. This shift can be along the surface normal $n_{kj}$ onto the surface in the approximation point $a_{kj}$. Alternatively, the shift of the approximation point $a_{kj}$ could also be in another direction, as has already been indicated above. A preferred variant of the shifting of the approximation points comprises carrying out this shifting at a predetermined step width. Alternatively, it may also be favorable to shift the approximation points proportionally to the difference between the reference velocity $v_R$ and the corrected velocity.

Figure 3:
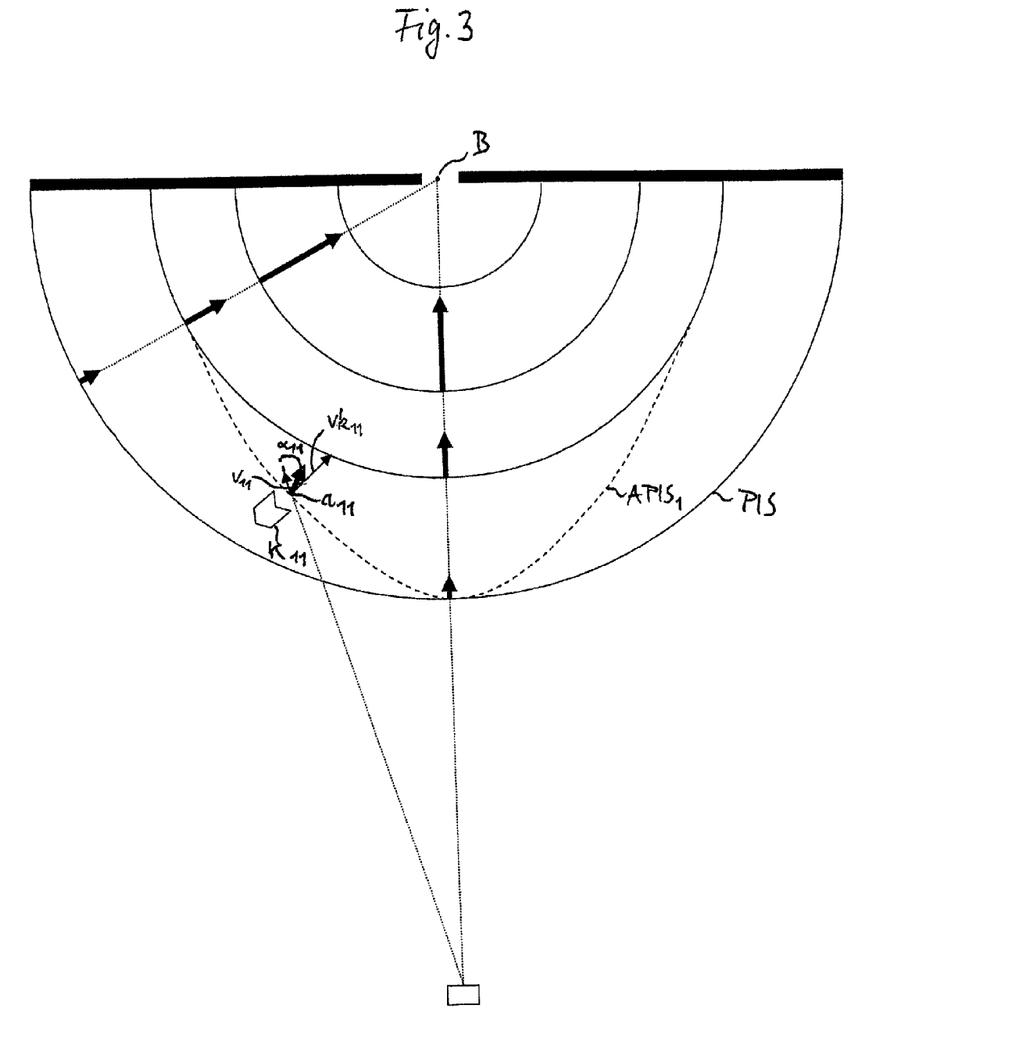

Then, in a step S9, a new approximation surface $APIS_{k+1}$ is acquired, which is shown in FIG. 3 and denoted by $APIS_1$. Said new approximation surface, on the one hand, can have any representation and, e.g. comprise a spline model. On the other hand, it can also include the shifted approximation points or a corresponding approach towards said approximation points.

Figure 4:
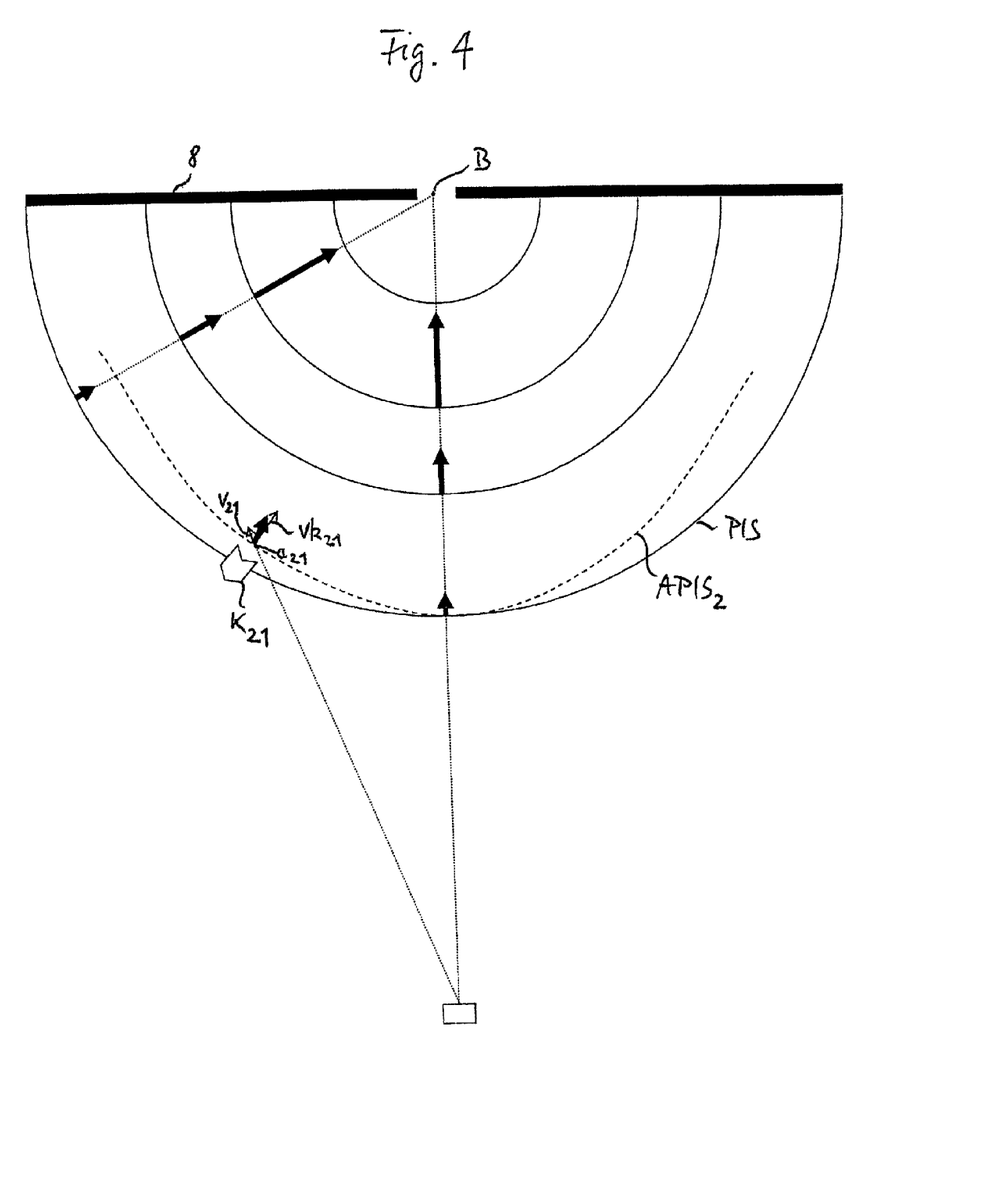
Figure 5:
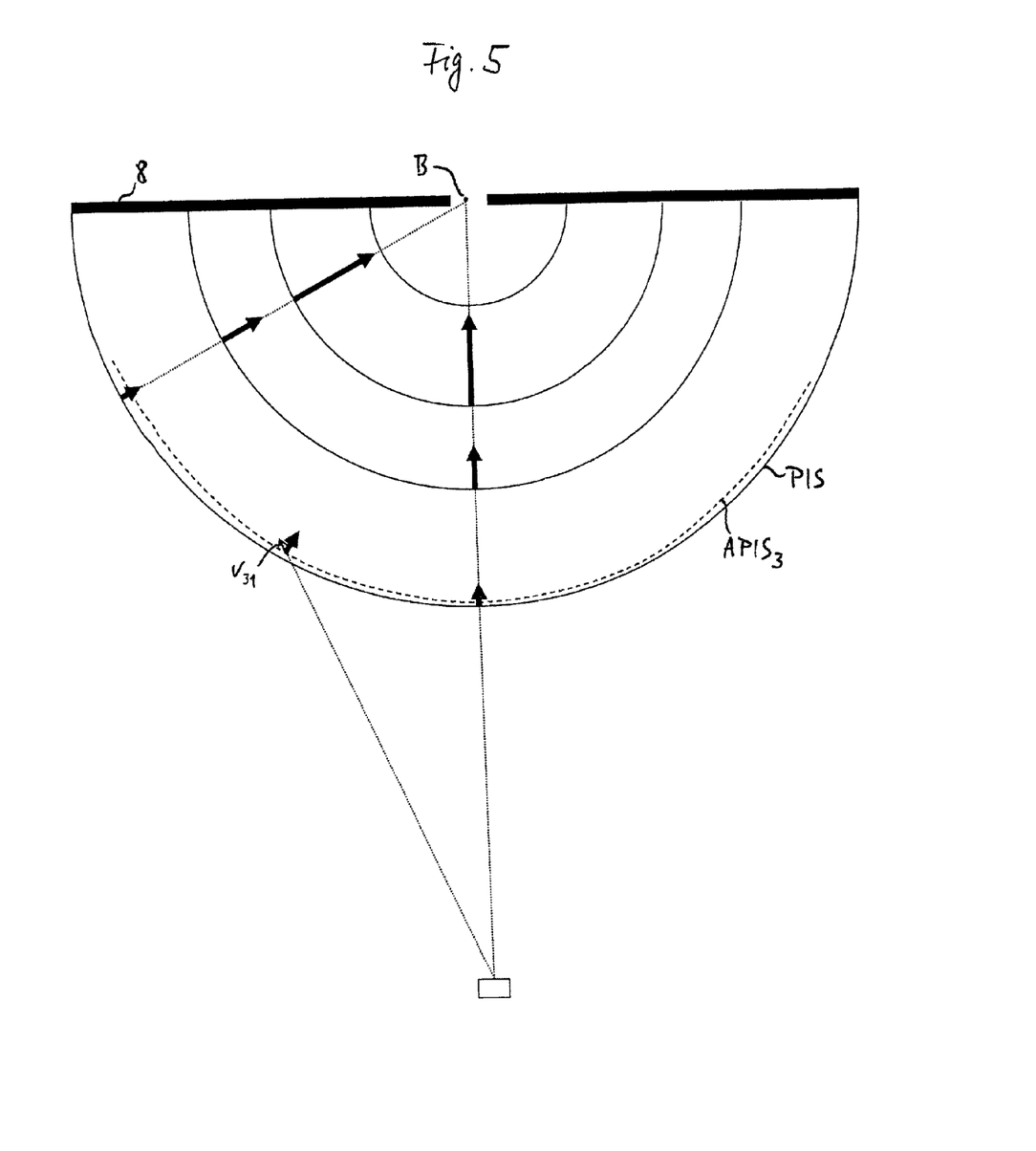

Then, by means of a return of the process to step S3 and a further run through steps S4-S9, the iteration goes on as long as is exemplary shown in FIGS. 4 and 5 until the iteration converges. To this end, for example in a step S10, it is checked whether the change of the new approximation surface APIS$_{k+1}$ compared to the old approximation surface APIS$_k$ is sufficiently minimal. This criterion, for example, can comprise the sum of the—possibly square—deviations between the shifted and the non-shifted approximation points a$_{kj}$, or in a spline model the sum of the changes of the supporting points, is smaller than a predetermined value ϵ.

The situation shortly before the convergence is reached is shown in FIG. 5. It can be seen that the assumption that the direction of the velocity is perpendicular to the surface becomes increasingly precise. Thus, also the velocity after the correction gets more and more precise. Thus, it can be taken from FIG. 5 that the approximation surface APIS$_3$ has already come very close to the true PIS.

Comparing FIGS. 4 and 5 with FIGS. 2 and 3, it becomes apparent that the APIS$_2$ and APIS$_3$, at the edges, i.e. in the area of the largest angle distance from the central beam, extend further towards the "top", i.e. towards the mitral valve 8. This is due to the fact that only when the iteration has progressed, it becomes possible to measure the velocity at the edge, since then the required correction angles are below the aforementioned limit of about 45°. The initial apparent progress of the PIS at the edge usually cannot be measured, but has to be determined by interpolation or extrapolation, respectively. Thus, in this area, in the course of the iteration, additional approximation points can be acquired so as to improve the accurateness of the approached or iterated approximation surface or their completeness, respectively.

The process thus goes through steps S3-S10 until the change of the new approximation surface APIS$_{k+1}$ compared to the old approximation surface APIS$_k$ is sufficiently minimal. Then, the approximation surface APIS$_{k+1}$ which was determined last is assumed to be the true proximal isokinetic shell PIS, which is done in a step S11. Then, in a step S12, the area A denoted by PISA of the PIS is determined; thereafter, in a step S13, the final result is multiplied by the reference velocity v$_R$ in order to calculate the flow through the opening in the observation area B. Then, in a step S14, both the iteratively derived PIS can be represented visually and the values for the PISA and the flow can be displayed on the monitor 16.

Figure 6:
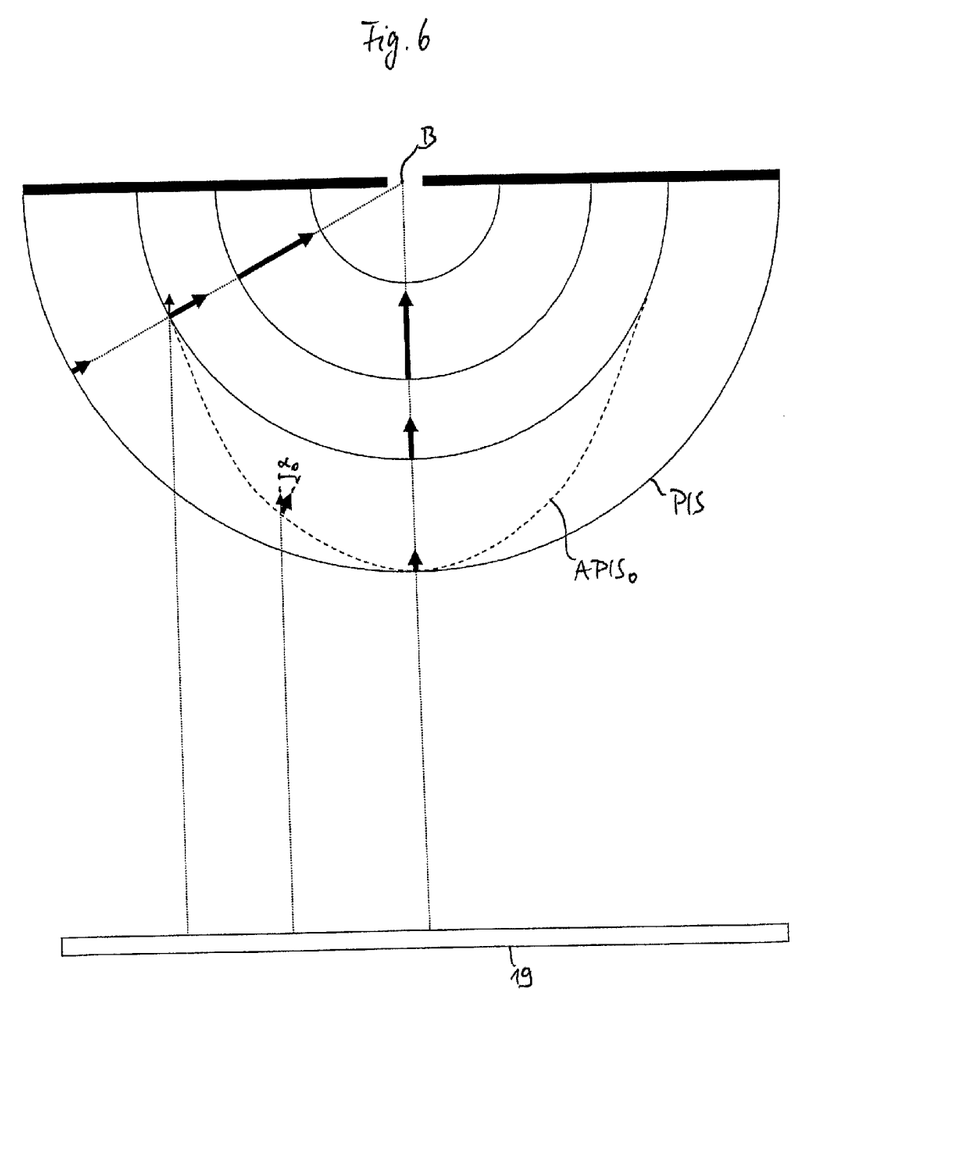

FIG. 6 depicts a second embodiment of the device according to the invention. It differs from the first embodiment in that instead of a sector color Doppler ultrasonic head 18 a linear color Doppler ultrasonic head 19 is used. As can be taken from FIG. 6, all measuring beams are parallel to each other as a result, while they spanned a sector of a circle in the first embodiment. Therefore, also a differently shaped apparent PIS is generated or, practically speaking, a different approximation surface APIS$_0$ is generated since the projections of the respective velocities onto the measurement directions are different than in the first embodiment. Thus, the angles of difference are also different. However, the course of the iteration process to determine the true PIS as well as its display and the calculation of the flow in the proximal convergence zone are essentially identical to the first embodiment and need not be explained again.

It is obvious that the velocity data cannot only be acquired according to the above exemplary description by means of ultrasound measurements, but e.g. also by means of MR phase-contrast measurements or laser interferometry.

It has to be noted that features of the invention described with reference to the embodiments shown and described, such as the type, design and acquisition of the individual approximation surfaces or details of the shifting or acquisition of the approximation points, can also be present in other embodiments, unless indicated otherwise or self-forbidding for technical reasons.

The invention claimed is:

1. A method of measuring flow rate of blood in human body using a color Doppler ultrasound device and an adaptive three-dimensional derivation of a proximal isokinetic shell of a proximal flow convergence zone that forms in an observation area in the blood, wherein magnitude of a velocity of the blood at each point of the proximal isokinetic shell is the same, the method comprises the steps of:
   a) obtaining locally distributed velocity measurements in an area surrounding the observation area using the color Doppler ultrasound device, said velocity measurements representing at least one directional component of the local velocity of the blood in a respective measurement direction,
   b) selecting one of the velocity values obtained in step (a) as a velocity reference value,
   c) preparing an approximation surface as an initial proximal isokinetic shell in such a way that the entire flow, at least substantially, in the flow convergence zone penetrates the approximation surface,
   d) establishing a plurality of approximation points on the approximation surface,
   e) determining a velocity measurement v$_{kj}$ at each approximation point,
   f) calculating a corrected velocity vk$_{kj}$ at each approximation point as a function of the velocity measurement at the respective approximation point, the respective measurement direction; and a surface normal at the respective approximation point,
   g) determining a correction direction by comparing the corrected velocity with the velocity reference value,
   h) shifting the approximation points in the respective correction direction to new positions, if necessary,
   i) acquiring a new approximation surface such that the new approximation surface at least approaches the new positions of the approximation points, and
   j) repeating steps d) through i) until the change of the new approximation surface is sufficiently minimal compared to the old approximation surface,
   k) determining surface area of the new approximation surface acquired in step (j),
   l) calculating the flow rate of blood by multiplying the surface area of the new approximation surface by the velocity reference value.

2. The method according to claim 1, wherein in order to calculate the corrected velocity vk$_{kj}$ the respective differential angle α$_{kj}$ between the respective measurement direction and a respective surface normal onto the approximation surface at the approximation points is considered.

3. The method according to claim 2, wherein the calculation of the corrected velocity in step e) is based on the following formula: vk$_{kj}$=v$_{kj}$/cos(α$_{kj}$).

4. The method according to claim 2, wherein in order to calculate the corrected velocity the respective differential angle is reduced for increasing iteration by a decreasing value of correction.

5. The method according to claim 1, wherein in step g) the correction direction points away from the flow convergence zone if the corrected velocity is larger than the velocity reference value, and points towards the flow convergence zone if the corrected velocity is smaller than the velocity reference value.

6. The method according to claim 1, wherein in step g) no correction is made if the difference between the corrected velocity and the velocity reference value is within a certain tolerance range.

7. The method according to claim 1, wherein each approximation point in step h) is shifted with a predetermined step width or proportionally to the difference between the reference velocity and the corrected magnitude of the velocity or along the respective surface normal onto the approximation surface.

8. The method according to claim 1, wherein in the course of the iteration in step d) the number of approximation points is increased compared to the preceding iteration step so as to acquire, on the edge of the new approximation surface, which edge is due to angle restrictions in the determination of the respective velocity, additional approximation points to enlarge the angle range covered by the approximation surface.

9. The method according to claim 1, wherein locally distributed velocity measurements are determined using pulsed ultrasound beams at a plurality of measurement angles.

10. A device for measuring flow rate of blood in human body using adaptive three-dimensional derivation of a proximal isokinetic shell of a proximal flow convergence zone that forms in an observation area in the blood, wherein magnitude of velocity of the blood at each point of the proximal isokinetic shell is the same, and wherein device comprises:
   a color Doppler ultrasound device configured to obtain locally distributed velocity measurements in an area surrounding the observation area, said velocity measurements representing at least one directional component of the local velocity of the blood in a respective measurement direction;
   a control and evaluation system configured to execute a series of steps comprising
      a) selecting one of the velocity measurement values obtained by the color Doppler ultrasound device as a velocity reference value,
      b) preparing an approximation surface as an initial proximal isokinetic shell in such a way that the entire flow, at least substantially, in the flow convergence zone penetrates the approximation surface,
      c) establishing a plurality of approximation points on the approximation surface,
      d) determining a velocity measurement $v_{kj}$ at each approximation point,
      e) calculating a corrected velocity $vk_{kj}$ at each approximation point as a function of the velocity measurement at the respective approximation point, the respective measurement direction; and a surface normal at the respective approximation point,
      f) determining a correction direction by comparing the corrected velocity with the velocity reference value,
      g) shifting the approximation points in the respective correction direction to new positions, if necessary,
      h) acquiring a new approximation surface such that the new approximation surface at least approaches the new positions of the approximation points, and
      i) repeating steps (c) through (h) until the change of the new approximation surface is sufficiently minimal compared to the old approximation surface,
      j) determining surface area of the new approximation surface acquired in step (i),
      k) calculating the flow rate of blood by multiplying the surface area of the new approximation surface by the velocity reference value; and
   a non-transitory storage means configured to store the velocity measurements obtained by the color Doppler ultrasound device, the velocity reference value, at least one approximation surface of the proximal isokinetic shell, and the plurality of approximation points.

11. The device according to claim 10, further comprising a display device for displaying the at least one approximation surface and the proximal isokinetic shell.

12. A non-transitory computer readable medium comprising a set of instructions that when executed by a computer processor, result in a series of steps being performed which carry out a method of measuring flow rate of blood in human body, using adaptive three-dimensional derivation of a proximal isokinetic shell of a proximal flow convergence zone that forms in an observation area in the blood, wherein magnitude of velocity of the blood at each point of the proximal isokinetic shell is the same, the method comprises the steps of:
   a) storing locally distributed velocity measurements in an area surrounding the observation area obtained using a color Doppler ultrasound device, said velocity measurements representing at least one directional component of the local velocity of the blood in a respective measurement direction,
   b) selecting one of the velocity values obtained in step (a) as a velocity reference value,
   c) preparing an approximation surface as an initial proximal isokinetic shell in such a way that the entire flow, at least substantially, in the flow convergence zone penetrates the approximation surface,
   d) establishing a plurality of approximation points on the approximation surface,
   e) determining a velocity measurement $v_{kj}$ at each approximation point,
   f) calculating a corrected velocity $vk_{kj}$ at each approximation point as a function of the velocity measurement at the respective approximation point, the respective measurement direction; and a surface normal at the respective approximation point,
   g) determining a correction direction by comparing the corrected velocity with the velocity reference value,
   h) shifting the approximation points in the respective correction direction to new positions, if necessary,
   i) acquiring a new approximation surface such that the new approximation surface at least approaches the new positions of the approximation points, and
   j) repeating steps d) through i) until the change of the new approximation surface is sufficiently minimal compared to the old approximation surface,
   k) determining surface area of the new approximation surface acquired in step (j),
   l) calculating the flow rate of blood by multiplying the surface area of the new approximation surface by the velocity reference value.

* * * * *